United States Patent [19]

Bedekovic

[11] Patent Number: 5,387,694
[45] Date of Patent: Feb. 7, 1995

[54] CHROMOGENIC METHYLENEPYRROLINES

[75] Inventor: Davor Bedekovic, Biel-Benken, Switzerland

[73] Assignee: Ciba-Geigy Corporation, Ardsley, N.Y.

[21] Appl. No.: 52,301

[22] Filed: Apr. 23, 1993

[30] Foreign Application Priority Data

Apr. 30, 1992 [CH] Switzerland .......... 1388/92

[51] Int. Cl.$^6$ .......................... C07D 209/44
[52] U.S. Cl. ................. 548/458; 548/364.7; 548/440; 548/466; 548/471
[58] Field of Search ........... 548/364.7, 440, 458, 548/466, 471

[56] References Cited

U.S. PATENT DOCUMENTS

| | | | |
|---|---|---|---|
| 4,356,123 | 10/1982 | Lotsch | 548/460 |
| 4,373,102 | 2/1983 | Neumann et al. | 544/143 |
| 4,385,174 | 5/1983 | Iqbal et al. | 542/417 |
| 4,481,272 | 11/1984 | Eckell et al. | 430/58 |
| 4,496,727 | 1/1985 | Iqbal et al. | 544/225 |

FOREIGN PATENT DOCUMENTS

| | | |
|---|---|---|
| 015570 | 3/1979 | European Pat. Off. |
| 036388 | 3/1980 | European Pat. Off. |
| 017132 | 10/1980 | European Pat. Off. |
| 061094 | 3/1981 | European Pat. Off. |
| 209028 | 1/1987 | European Pat. Off. |
| 298037 | 1/1989 | European Pat. Off. |

OTHER PUBLICATIONS

Patent Abst's. of Japan vol. 001, No. 317 (1987) of JP-A-62106076.
Derwent Abst. 89-009254/02 of EP 298,037 (1989).
Derwent Abst. 87-015773/03 of EP 209,028 (1987).

*Primary Examiner*—Richard L. Raymond
*Attorney, Agent, or Firm*—George Dohmann

[57] ABSTRACT

The present invention relates to chromogenic methylenepyrrolines and processes and intermediates for their preparation and to their use.

The chromogenic methylenepyrroline compounds according to the invention have the formula (I) defined in claim 1.

These colour formers are suitable in particular for thermographic recording processes and produce intensive red, violet, blue or brown colourations. They are distinguished by the fact that they do not require any conventional electron-withdrawing acid colour developer.

16 Claims, No Drawings

CHROMOGENIC METHYLENEPYRROLINES

The present invention relates to chromogenic methylenepyrrolines and processes for their preparation and to their use.

The chromogenic methylenepyrroline compounds according to the invention have the general formula

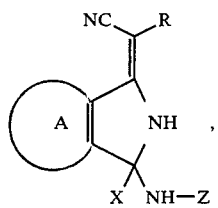 (I)

in which

X is pyrrolyl, thienyl, indolyl, carbazolyl, acridinyl, pyrazolonyl, benzofuranyl, benzothienyl, naphthothienyl, phenothiazinyl, indolinyl, julolidinyl, kairolinyl, dihydroquinolinyl, tetrahydroquinolinyl, a phenyl or naphthyl radical which is unsubstituted or substituted by up to three identical or different substituents from the group consisting of halogen, cyano, lower alkyl, $C_5$–$C_6$cycloalkyl, $C_1$–$C_8$acyl, —$NR_1R_2$, —$OR_3$ or—$SR_3$, R is CN or substituted or unsubstituted phenylcarbarnoyl, Z is an acyl radical, and A is a radical for forming an aromatic or heterocyclic ring having 6 ring atoms, it being possible not only for ring A but also for the fused-on ring to be substituted.

X as heteroaromatic radical in formula (I) is preferably bound to the carbon atom of the pyrroline compound via a carbon atom of the hetero ring.

The mono- or polynuclear heteroaromatic radical can be ring-mono- or-poly-substituted. Examples of suitable C substituents are halogen, hydroxyl, cyano, nitro, lower alkyl, lower alkenyl, lower alkoxy, lower alkylthio, lower alkoxycarbonyl, acyl having 1 to 8 carbon atoms, preferably lower alkylcarbonyl, amine, lower alkylamino, lower alkylcarbonylamino or di(-lower alkyl)amino, $C_5$–$C_6$cycloalkyl, benzyl or phenyl, while examples of N substituents are $C_1$–$C_{12}$alkyl, $C_2$–$C_{12}$alkenyl, $C_5$–$C_{10}$cycloalkyl, $C_1$–$C_8$acyl, phenyl, benzyl, phenethyl or phenylisopropyl, each of which can be substituted, for example, by cyano, halogen, nitre, hydroxyl, lower alkyl, lower alkoxy, lower alkylamino or lower alkoxycarbonyl.

The alkyl and alkenyl radicals can be straight-chain or branched. Examples of these are methyl, ethyl, n-propyl, isopropyl, n-butyl, 1-methylbutyl, sec-butyl, t-butyl, amyl, isopentyl, n-hexyl, 2-ethylhexyl, isooctyl, n-octyl, 1,1,3,3-tetramethylbutyl, nonyl, isononyl, 3-ethylheptyl, decyl or n-dodecyl or vinyl, allyl, 2-methylallyl, 2-ethylallyl, 2-butenyl or octenyl. Lower alkenyl radicals are bound to heteroatoms, in particular nitrogen, via a saturated carbon atom.

As substituent of the radical X, "acyl" is in particular formyl, lower alkylcarbonyl, for example acetyl or propionyl, or benzoyl. Further acyl radicals can be lower alkylsulfonyl, for example methylsulfonyl or ethylsulfonyl, and phenylsulfonyl. Benzoyl and phenylsulfonyl can be substituted by halogen, methyl, methoxy or ethoxy.

Lower alkyl, lower alkoxy and lower alkylthio are those groups or group components having 1 to 12, preferably 1 to 6, in particular 1 to 3, carbon atoms. Examples of such groups are methyl, ethyl, n-propyl, isopropyl, n-butyl, sec-butyl, tert-butyl, amyl, isoamyl or hexyl, and methoxy, ethoxy, isopropoxy, isobutoxy, tert-butoxy or amyloxy, and methylthio, ethylthio, propylthio or butylthio.

Examples of halogen are fluorine, bromine or, preferably, chlorine.

Preferred heteroaromatic radicals are pyrrolyl, pyrazolonyl, indolyl or carbazolyl radicals, in particular substituted 2- or 3-pyrrolyl or, especially, 3-indolyl radicals, for example N—$C_1$–$C_8$alkylpyrrol-2-yl, 2-phenylindol-3-yl, 2-methylindol-3-yl, N—$C_1$–$C_8$alkyl-2-methyl-indol-3-yl, N—$C_2$–$C_4$alkanoyl-2-methylindol-3-yl, 2-phenylindol-3-yl or N—$C_1$–$C_8$alkyl-2-phenylindol-3-yl radicals.

As aromatic radical, X can be a phenyl or naphthyl radical which is unsubstituted or substituted by up to three identical or different substituents from the group consisting of halogen, cyano, lower alkyl, $C_5$–$C_6$cycloalkyl or $C_1$–$C_8$acyl, —$NR_1R_2$, —$OR_3$ or —$SR_3$.

As aromatic radical, X is preferably a substituted phenyl radical of the formula

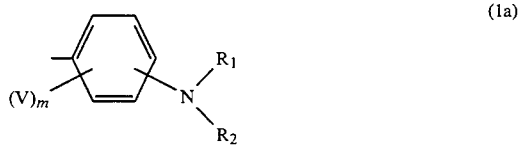 (1a)

or

 (1b)

in which $R_1$, $R_2$ and $R_3$, independently of one another, are hydrogen, unsubstituted or halogen-, hydroxyl-, cyano- or (lower alkoxy)-substituted alkyl having at most 12 carbon atoms, acyl having 1 to 8 carbon atoms, cycloalkyl having 5 to 10 carbon atoms or unsubstituted or halogen-, trifluoromethyl-, cyano-, (lower alkyl)-, (lower alkoxy)-, (lower alkoxycarbonyl)-, —NX'X"—or 4-NX'X"-phenylamino-ring-substituted phenylalkyl or phenyl, X' and X", independently of one another, are hydrogen, lower alkyl, cyclohexyl, benzyl or phenyl or $R_1$ and $R_2$ together with the nitrogen atom linking them are a five- or six-membered, preferably saturated, heterocyclic radical, V is hydroxyl, halogen, lower alkyl, $C_1$–$C_{12}$alkoxy, $C_5$–$C_7$cycloalkoxy, $C_1$–$C_{12}$acyloxy, benzyl, phenyl, benzyloxy or phenoxy each of which is unsubstituted or substituted in the phenyl radical by halogen, cyano, lower alkyl or lower alkoxy, or, in the case of the phenyl radical of formula (1a), also the group —$NT_1T_2$, $T_1$ and $T_2$, independently of one another, are hydrogen, lower alkyl, $C_5$–$C_{10}$cycloalkyl, unsubstituted or halogen-, cyano-, (lower alkyl)- or (lower alkoxy)-substituted benzyl, or acyl having 1 to 8 carbon atoms and $T_1$ is also unsubstituted or halogen-, cyano-, (lower alkyl)- or (lower alkoxy)-substituted phenyl, and m is 0, 1 or 2.

The substituents —NR₁R₂ and —OR₃ are preferably in the paraposition, relative to the point of linkage. V is preferably in the ortho position, relative to the point of linkage.

Examples of $R_1$, $R_2$ and $R_3$ as alkyl are the substituents listed above for alkyl radicals.

Substituted alkyl radicals in $R_1$, $R_2$ and $R_3$ are in particular cyanoalkyl, haloalkyl, hydroxyalkyl, alkoxyalkyl, each preferably having a total of 2 to 8 carbon atoms, for example 2-cyanoethyl, 2-chloroethyl, 2-hydroxyethyl, 2-methoxyethyl, 2-ethoxyethyl, 2,3-dihydroxypropyl, 2-hydroxy-3-chloropropyl, 3-methoxypropyl, 4-methoxybutyl or 4-propoxybutyl.

Examples of $R_1$, $R_2$, $R_3$, $T_1$ and $T_2$ as cycloalkyl are cyclopentyl, cycloheptyl or, preferably, cyclohexyl. The cycloalkyl radicals can contain one or more $C_1$-$C_4$alkyl radicals, preferably methyl groups, and have a total of 5 to 10 carbon atoms.

$R_1$, $R_2$ and $R_3$ as aralkyl or phenylalkyl can be phenethyl, phenylisopropyl or, in particular, benzyl.

Examples of preferred substituents in the phenylalkyl and phenyl group of $R_1$, $R_2$ and $R_3$ are halogen, cyano, methyl, trifluoromethyl, methoxy or carbomethoxy. Examples of such araliphatic or aromatic radicals are methylbenzyl, 2,4- or 2,5-dimethylbenzyl, chlorobenzyl, dichlorobenzyl, cyanobenzyl, tolyl, xylyl, chlorophenyl, methoxyphenyl, 2,6-dimethylphenyl, trifluoromethylphenyl or carbomethoxyphenyl.

The acyloxy radical in V is, for example, formyloxy, lower alkylcarbonyloxy, for example acetyloxy or propionyloxy, or benzyloxy. As $C_1$-$C_{12}$alkoxy radical, V can be a straight-chain or branched group, for example methoxy, ethoxy, isopropoxy, n-butoxy, tert-butoxy, amyloxy, 1,1,3,3-tetramethylbutoxy, n-hexyloxy, n-octyloxy or dodecyloxy. Examples of V as cycloalkoxy are cyclopentyloxy, cycloheptyloxy or, preferably, cyclohexyloxy.

A heterocyclic radical formed by the pair of substituents ($R_1$ and $R_2$) together with the common nitrogen atom is, for example, pyrrolidino, piperidino, pipecolino, morpholino, thiomorpholino, piperazino, N-alkylpiperazino, for example N-methylpiperazino, N-phenylpiperazino or N-alkylimidazolino. Preferred saturated heterocyclic radicals for —NR₁R₂ are pyrrolidino, piperidino or morpholino.

Substituents $R_1$ and $R_2$ are preferably cyclohexyl, benzyl, phenethyl, cyano (lower alkyl), for example β-cyanoethyl or, especially, lower alkyl, for example methyl, ethyl, n-pentyl or, in particular, n-butyl. —NR₁R₂ is preferably also pyrrolidinyl. $R_3$ is preferably lower alkyl or benzyl.

Advantageously, V can be hydrogen, hydroxyl, halogen, lower alkyl, $C_1$-$C_8$alkoxy, preferably lower alkoxy, benzyloxy, for example methyl, methoxy, ethoxy, isopropoxy or n-butoxy, or the group —NT₁T₂, one of the radicals $T_1$ and $T_2$ being preferably $C_1$-$C_8$acyl or lower alkyl and the other being hydrogen or lower alkyl. In this case, the acyl radical is in particular lower alkylcarbonyl, for example acetyl or propionyl. V is preferably acetylamino, dimethylamino, diethylamino, hydroxyl, benzyloxy or, in particular, lower alkoxy and, especially, ethoxy or n-butoxy.

Z as acyl radicals are substituents on the nitrogen atom which can be detached thermally, advantageously above. 100° C. Substituents of this type can be aliphatic, cycloaliphatic, araliphatic, aromatic or heterocyclic acyl groups of, for example, the formula (1c) $Y-(Q_1)_n-Q_2-$, in which Y is an organic radical, preferably unsubstituted or substituted $C_1$-$C_{22}$alkyl, aryl, cycloalkyl, aralkyl or heteroaryl, $Q_1$ is —NH— or oxygen, $Q_2$ is —CO— or —SO₂— and n is 0 or 1, preferably 0.

Examples of suitable acyl groups Z are acetyl, 2,2-dimethylpropionyl, propionyl, chloroacetyl, caproyl, capryloyl, benzoyl, chlorobenzoyl, methylbenzoyl, tert-butylbenzoyl, methylsulfonyl, ethylsulfonyl, chloroethylsulfonyl, ethoxycarbonyl, trifluoromethylsulfonyl, 2-chloroethylsulfonylacetyl, phenylsulfonyl, tolylsulfonyl, ethylaminocarbonyl or phenylaminocarbonyl.

Z is preferably an acyl group of the formula Y'—CO, in which Y' is $C_3$-$C_8$alkyl or phenyl. Alkyl can be straight-chain or branched.

Ring A can be a fused aromatic ring, for example a naphthalene, quinoline or quinoxaline ring, or, preferably, a benzene ring. As 6-membered heterocyclic ring, A is in particular a nitrogen-containing heterocycle of aromatic character, for example a pyridine or pyrazine ring. Not only the aromatic ring but also the nitrogen-containing heterocycle can be unsubstituted or substituted by halogen, cyano, nitro, lower alkyl, lower alkoxy, lower alkylthio, lower alkylcarbonyl, lower alkoxycarbonyl, amino, lower alkylamino, di(lower alkyl)amino or lower alkylcarbonylamino. In a particularly preferred embodiment, ring A is a benzene ring which is unsubstituted or substituted by halogen, methyl, methoxy, butoxy, dimethylamino or diethylamino.

The preferred 6-membered aromatic or heterocyclic radicals represented by A are 2,3-pyridino, 3,4-pyridino, 2,3-pyrazino, 2,3-quinoxalino, 1,2-naphthaleno, 2,3-naphthaleno or 1,2-benzo, each of which is unsubstituted or substituted by halogen, such as chlorine or bromine, nitro, lower alkyl, lower alkoxy, lower alkylthio or a substituted or unsubstituted amino group defined as above, a 1,2-benzo radical which is unsubstituted or substituted by halogen, methyl, methoxy, butoxy, dimethylamino or diethylamino being particularly preferred.

Substituent R as phenylcarbamoyl is in particular a radical of the formula

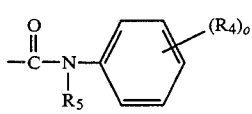
(1d)

in which each $R_4$, independently of the others, is hydroxyl, halogen, nitro, cyano, acyl having 1 to 8 carbon atoms, lower alkyl or lower alkoxy which is unsubstituted or substituted by halogen, hydroxyl, cyano or lower alkoxy, $R_5$ is hydrogen or lower alkyl and o is 0, 1, 2 or 3.

Preference is given to isoindolines of the formula

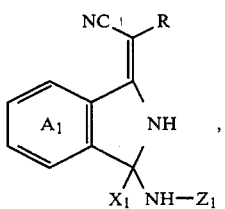

in which
A$_1$ is unsubstituted or substituted by halogen, cyano, lower alkyl, lower alkoxy or di(lower alkyl)amino, Z$_1$ is C$_1$–C$_{12}$alkyl—CO— or benzoyl which is unsubstituted or substituted by halogen, nitro, lower alkyl or lower alkoxy and X$_1$ is a 3-indolyl radical of the formula

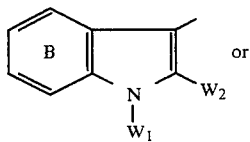

a substituted phenyl radical of the formula

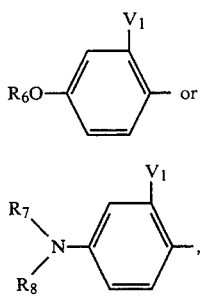

W$_1$ is hydrogen, unsubstituted or cyano- or (lower alkoxy)-substituted C$_1$–C$_8$alkyl, acetyl, propionyl or benzyl, W$_2$ is hydrogen, lower alkyl, in particular methyl, or phenyl, R$_6$, R$_7$ and R$_8$, independently of one another, are each unsubstituted or hydroxyl-, cyano-or (lower alkoxy)-substituted alkyl having at most 12 carbon atoms, C$_5$–C$_6$cycloalkyl, benzyl, phenethyl or phenyl and R$_6$ is also hydrogen, or (R$_5$ and R$_6$) together with the nitrogen atom linking them are pyrrolidino, piperidino or morpholino, V$_1$ is hydrogen, hydroxyl, halogen, lower alkyl, C$_1$–C$_8$alkoxy, benzyloxy or the group —NT$_3$T$_4$, T$_3$ and R$_4$, independently of one another, are each hydrogen, lower alkyl, lower alkylcarbonyl or unsubstituted or halogen-, methyl- or methoxy-substituted benzoyl R is cyano or a substituted or unsubstituted radical of the formula

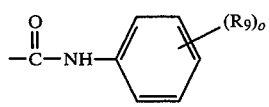

R$_9$ is halogen or lower alkyl,
o is 0, 1 or 2 and
B is unsubstituted or substituted by halogen, lower alkyl, such as methyl or isopropyl, or by di(lower alkyl)amino, such as dimethylamino. Of the compounds of the formula (I), isoindoline compounds in which X$_1$ is a 3-indolyl radical of the formula (2a), W$_1$ is hydrogen or C$_1$–C$_8$alkyl, W$_2$ is methyl or phenyl, and Z$_1$ is C$_3$–C$_8$alkylcarbonyl are particularly preferred.

Particular mention may be made of
a) dicyanoisoindolines of the formula

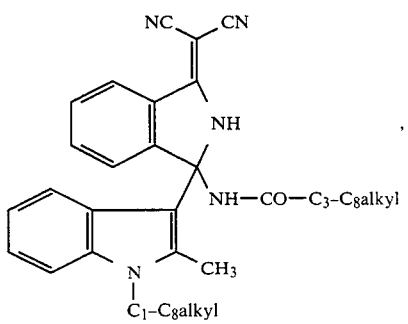

b) dicyanoisoindolines of the formula

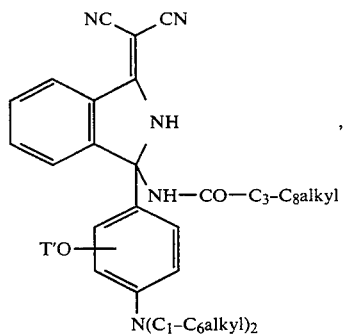

in which T' is hydrogen or C$_1$–C$_6$alkyl, c) dicyanoisoindolines of the formula

in which T' is hydrogen or C$_1$–C$_6$alkyl, d) isoindolines of the formula

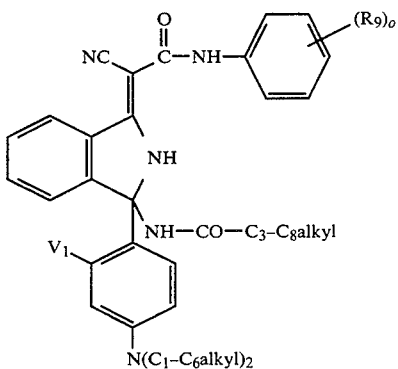

(Id)

in which
R$_9$ is halogen or lower alkyl,
o is 0, 1 or 2 and
V$_1$ is hydrogen or hydroxyl, or
e) isoindolines of the formula

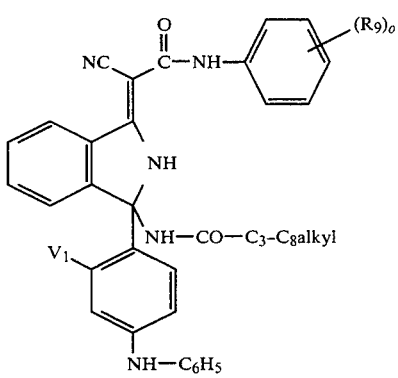

(Ie)

in which
R$_9$ is halogen, lower alkyl or lower alkoxy,
o is 0, 1 or 2 and
V$_1$ is hydrogen or hydroxyl.

The pyrrolines according to the invention of the formulae (I), (Ia), (Ib), (Ic), (Id) or (Ie) are prepared by subjecting a suitable aromatic or heteroaromatic compound
(II) X–H
in which
X is as defined above, to an addition reaction with a pyrroline derivative of the formula

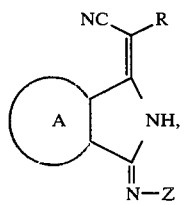

(III)

in which
A, R and Z are as defined above.

The addition reaction is carded out at a temperature of 15° to at most 70° C., preferably at room temperature (15°–30° C.). Advantageously, it takes place in organic solvents and, if desired, under the action of acid condensating agents.

Suitable solvents, which represent the reaction medium, are alcohols, for example methanol, ethanol, propanol, ethylene glycol monomethyl ether or ethylene glycol monoethyl ether, ketones, for example acetone, butanone or methyl isopropyl ketone, dimethylformamide, dimethyl sulfoxide or nitriles of aliphatic monocarboxylic acids, for example acetonitrile, propiontrile or butyronitrile, cycloaliphatic or aromatic hydrocarbons, for example cyclohexane, benzene, toluene or xylene; chlorinated hydrocarbons, for example ethylene chloride, tetrachloroethylene or chlorobenzenes, for example monochlorobenzene, monochlorotoluene or dichlorobenzene, or cyclic ethers, for example dioxane or tetrahydrofuran.

Preferred solvents are methanol, acetone, methyl ethyl ketone and toluene and-mixtures thereof.

Examples of acid condensating agents which can be used are phosphoric acid, sulfuric acid, hydrochloric acid, acetic acid, trifluoroacetic acid, propionic acid and, in particular, p-toluenesulfonic acid, fluorobenzoic acid, nitrobenzoic acid, benzoic acid and trichloroacetic acid.

The duration of the addition reaction depends on the condensating agent, the solvent and the addition compound used and is usually between 2 and 10 hours, preferably 2.5 and 6 hours.

After the addition reaction, the chromogenic dicyanomethylenepyrroline compound obtained is isolated in the usual manner, for example by removing the solvent by distillation, then filtering off the precipitated pyrroline compound and drying it. If necessary, the pyrroline compound can be purified by recrystallisation in, for example, toluene.

Particularly preferred addition compounds are anilines, such as cresidines, phenetidines, 3-butoxyanilines, N,N-dialkylaminophenols, and 2-(lower alkyl)indoles or 2-phenylindoles, each of which can be N-substituted by C$_1$–C$_8$alkyl.

Specific examples of addition compounds of the formula (II) are N,N-dimethylaniline, N,N-diethylaniline, N,N-dibenzylaniline, N-phenylpyrrolidine, N,N-dibutylaniline, N-methyl-N-cyclohexylaniline, 3-methoxyN,Ndimethylaniline, 3-ethoxy-N,Ndiethylaniline, 3-ethoxy-N,N-di-n-pentylaniline, 3-n-butoxy-N,N-di-n-butylaniline, 3-acetylaminoN,N-dipropylaniline, 2-methyl-5-hydroxy-N-ethylaniline (3-ethylamino-4-cresol), 3-hydroxydiphenylamine, 4-ethoxydiphenylamine, 3-ethoxy-N,N-dimethylaniline, 3-hydroxy-N,N-dimethylaniline, 3-hydroxy-N,N-diethylaniline, 3-hydroxy-N,N-di-n-butylaniline, 2-methylindole, 2-phenylindole, 1,2-dimethylindole, 1-ethyl-2-methylindole, 1-n-butyl-2-methylindole, 1-n-octyl-2-methylindole, N-butylcarbazole, 3-methyl-6-dimethylaminoindole, 3-methyl-6-ethoxyindole, 1-ethyl-3methyl-6-ethoxyindole, 1-phenyl-3-methyl-5-pyrazolone.

The compounds of the formula (III) in which R is cyano and which are required as starting materials are prepared, for example, by reaction of 1,3-diiminopyrroles, for example 1,3-diiminoisoindolines, with malononitrile, followed by introduction of the radical Z by acylation. Both the reaction with malononitrile and acylation are carded out in a known manner.

The compounds of the formula (III) are novel. They are valuable starting compounds for the colour formers according to the invention of the formula G). Accordingly, the invention also relates to the novel starting compounds of the formula

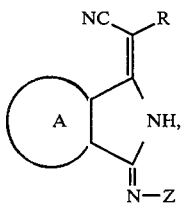

(III)

in which,

A, R and Z are as defined above.

Apart from relating to the compounds of the formula (III), the invention also relates to a process for the preparation of the novel compounds of the formula (III). The process comprises reacting an iminopyrrole of the formula

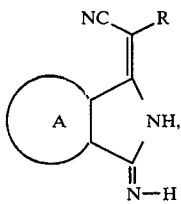

(IV)

in which A and R are as defined above, with a compound of the formula $$Y\text{—}(Q_1)_n\text{—}Q_2\text{—}Y,\qquad (V)$$

in which

Y is an organic radical, preferably substituted or unsubstituted $C_1$-$C_{22}$alkyl, aryl, cycloalkyl, aralkyl or heteroaryl, $Q_1$ is —NH— or oxygen $Q_2$ is —CO— or —SO$_2$— n is 0 or 1, preferably 0, and

Y is a nucleofugic group, preferably halogen.

The compounds of the formula (IV) are obtainable by reaction of diiminopyrroles of the formula

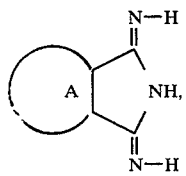

(VI)

in which A is as defined above, with a malononitrile, or a cyanoacetamide of the formula $$NC\text{—}CH_2Z,\qquad (VII)$$

in which Z is as defined above.

Examples of specific diiminopyrroles include 1,3-diiminoisoindole, 1,3-diimino-5-chloroisoindole, 1,3-diimino-4,5-dichloroisoindole, 1,3-diimino-5-methylisoindole, 1,3-diimino-5-tert-butylisoindole, 1,3-diimino-5-methoxyisoindole and 1,3-diimino-5-butoxyisoindole.

Acylation of the products obtained by reaction of 1,3-diiminoisoindolines with malononitrile can be carded out with carboxylic anhydrides, carbonyl halides or sulfonyl halides.

Suitable acylating agents are in particular carbonyl chlorides or carboxylic anhydrides of $C_2$-$C_{12}$alkanoic acids, benzoyl chloride and substitution products thereof, such as chlorobenzoyl chloride, methylbenzoyl chloride or tert-butylbenzoyl chloride.

Preferred acylating agents are trimethylacetyl chloride, caproyl chloride or capryloyl chloride.

The compounds according to the invention of the formulae (I), (Ia), (Ib), (Ic) or (Id) are suitable in particular as colour formers in a thermoreactive recording-material. They are distinguished by the fact that no conventional acid dye developers, for example clays, phenols, zinc salicylates or phenolic resins, are required for colour formation. The compounds according to the invention can also be used as transfer dyes, for example for the thermodiffusion transfer method.

The colour of the image obtained in the heat-sensitive recording material can be red, violet, blue or brown, depending on the definition of X. The images obtained are sharp and clear.

The heat-sensitive recording materials are used, for example, for recording information, for example in electronic computers, printers, fax or copying machines, telex machines or in medical or industrial recording instruments and measuring instruments, for example electrocardiographs, or for manufacturing labels or bar codes.

Image production (marking) can also take place manually by means of a heated pen. A further device for producing markings by means of heat are laser beams.

Advantageously, the heat-sensitive recording systems contain at least one base, for example paper, synthetic paper, a plastic sheet, and one or more heat-sensitive layers formed thereon and containing the dicyanomethylene compound of the formulae (I), (Ia), (Ib), (Ic) or (Id). If necessary, the heat-sensitive recording materials according to the invention can contain activators or sensitisers.

Preferably, meltable, film-forming binders are used for preparing the thermoreactive recording material. These binders are usually water-soluble, while dicyanomethylene compounds according to the invention are insoluble in water. The binder should be capable of dispersing and fixing the dicyanomethylene compound at room temperature.

Upon application of heat, the compound Z-NH$_2$ is eliminated from the dicyanomethylene compound, which acts as colour former, resulting in colour formation.

Examples of water-soluble or at least water-swellable binders are hydrophilic polymers, such as polyvinyl alcohol, alkali metal polyacrylates, hydroxyethylcellulose, methylcellulose, carboxymethylcellulose, polyacrylamide, polyvinylpyrrolidone, carboxylated butadiene/styrene copolymers, gelatine, starch or etherified cornstarch.

The thermoreactive layers can contain further additives. In order to improve whiteness or suitability for the thermal head and thus to facilitate printing of the papers and to prevent the heated pen from sticking to the paper, these layers can contain, for example, antioxidants, UV absorbers, solubilisers, talc, titanium dioxide, zinc oxide, alumina, aluminium hydroxide, calcium carbonate (for example chalk), magnesium carbonate, clays and also organic pigments, for example urea/formaldehyde polymers. For colour formation only within a limited temperature range, it is possible to add substances such as urea, thiourea, diphenylthiourea, acetamide, acetanilide, benzenesulfanilide, stearamide, triphenylmethane, p-benzylbiphenyl, phthalic anhydride, metal stearate, for example zinc stearate, phthalonitrile, dimethyl terephthalate or other suitable, meltable products inducing Z—$NH_2$ formation. The thermographic recording materials preferably contain waxes, for example Carnauba wax, Montan wax, paraffin wax, polyethylene wax, condensation products of higher fatty acid amides with formaldehydes and condensation products of higher fatty acids with ethylenediamine. If desired, the recording materials can also contain alkaline materials, for example hydroxides or carbonates of alkali metals or, preferably, open-chain or cyclic organic bases, such as amines, alkanolamines, guanidines, pyridines or imidazole derivatives.

In the examples which follow, the percentages and parts given are by weight unless stated otherwise.

A. Preparation Examples

Example 1:

1-Dicyanomethylene-3-(2,2-dimethylpropionylamino)-3-(2-methyl- 1-n-octylindol-3-yl)isoindoline 2.8 g of 1-dicyanomethylene-3-dimethylpropionyliminoisoindoline are stirred together with 2.43 g of 1-n-octyl-2-methylindole and 0.2 g of p-toluenesulfonic acid in 15 ml of toluene and 10 ml acetone at room temperature for 6 hours. This is followed by concentrating the solvent mixture, resulting in the formation of a precipitate. The precipitate is filtered off, washed with toluene and dried. 3 g of the compound of the formula

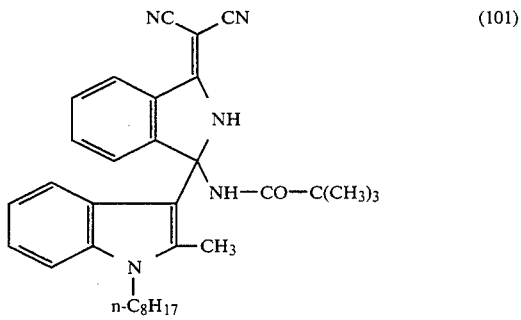

are isolated as colourless crystals having a melting point of 178°–179° C. In thermography, this colour former develops a red-violet marking.

The compounds of Table 1 are obtained analogously to Example 1.

In accordance with the embodiment in Example 1, the dicyanomethyleneisoindolines listed in the table below are obtained by using the corresponding reaction components and the addition reaction temperature. The last column of the table shows the colour obtained in thermography.

TABLE 1

Compounds of the formula (I)

| Example | Addition reaction temperature [°C.] | X″ | Alkyl | Yield in % | M.p./°C. | Colour developed |
|---|---|---|---|---|---|---|
| 2 | 20–25 | 2-methylindol-3-yl (N-H) | —$C(CH_3)_3$ | 71 | 212–215 | red-violet |
| 3 | 20–25 | 2-methylindol-3-yl (N-$C_2H_5$) | —$C(CH_3)_3$ | 46 | 165–167 | red-violet |
| 4 | 20–25 | 2-methylindol-3-yl (N-H) | —$(CH_2)_4$—$CH_3$ | 80 | 209–211 | red-violet |
| 5 | 20–25 | 4-$(C_4H_9)_2N$-2-hydroxyphenyl | —$(CH_2)_4$—$CH_3$ | 82 | 128–130 | blue |

TABLE 1-continued

Compounds of the formula (I)

$$\text{NC—C(=CR)—[benzene ring fused]—C(X'')(NH-COalkyl)-NH}$$

| Example | Addition reaction temperature [°C.] | X'' | Alkyl | Yield in % | M.p./°C. | Colour developed |
|---|---|---|---|---|---|---|
| 6 | 30–35 | 4-(C$_4$H$_9$)$_2$N-, 2-OC$_4$H$_9$-phenyl | —C(CH$_3$)$_3$ | 29 | 165–168 | blue |
| 7 | 20–25 | 4-(C$_4$H$_9$)$_2$N-, 2-OH-phenyl | —C(CH$_3$)$_3$ | 82 | 145–146 | blue |
| 8 | 60–65 | 4-(CH$_3$)$_2$N-phenyl | —C(CH$_3$)$_3$ | 25 | 140–150 | blue |
| 9 | 20–25 | 2-OH, 4-C$_2$H$_5$NH-phenyl | —C(CH$_3$)$_3$ | 60 | >210 | reddish blue |
| 10 | 20–25 | 2-OH, 4-(phenyl-NH)-phenyl | —C(CH$_3$)$_3$ | 43 | 107–109 | reddish blue |
| 11 | 20–25 | 3-methyl-2-phenyl-1H-indol-5-yl | —C(CH$_3$)$_3$ | 68 | 185–190 | red |
| 12 | 30–35 | 3-methyl-1-phenyl-5-oxo-pyrazol-4-yl | —C(CH$_3$)$_3$ | 53 | 110–120 | brown |

Example 13:

1-(α-cyano-α-[3,4-dichlorophenylaminocarbonyl]methylene)-3-(2,2-dimethylpropionyl-amino)-3-(4-dibutylamino-2-hydroxyphenyl)isoindoline 2.23 g of 1-(α-cyano-α-[3,4-dichlorophenylaminocarbonyl]methylene)-3-(2,2-dimethylpropionylamino)isoindole are stirred together with 1.02 g of dibutylaminophenol and 0.1 g of trichloroacetic acid in 20 ml of toluene at room temperature for 3 hours. The mixture is then additionally heated at 35°–40° C. for 1 hour until no more educt can be detected (thin-layer chromatography). The precipitated product is filtered off, washed with a small amount of toluene, and the crystals thus obtained are taken up in acetone, and the solution is purified with activated carbon. The acetone phase is concentrated, the precipitated crystals are washed with n-hexane and dried at room temperature in vacuo. 2.0 g of the title compound of the formula

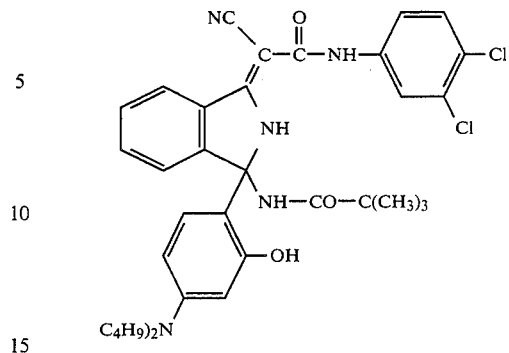
(113)

are isolated as beige-coloured crystals of melting point 168°–170° C. The compounds of Table 2 can be prepared analogously to the above preparation examples:

TABLE 2

Compounds of the formula (I)

| Comp. No. | X" | (R4)n | Phys. data | Colour[1] |
|---|---|---|---|---|
| 114 | (C4H9)2N—⌬—OH | 4-Cl | m.p. 108–12° C. | red-violet |
| 115 | C6H5NH—⌬—OH | 3,4-Cl2 | m.p. >210° C. | red-violet |
| 116 | C6H5NH—⌬—OH | 4-Cl | m.p. >220° C. | red-violet |
| 117 | C6H5NH—⌬—OH | 4-OCH3 | m.p >200° C. | violet |
| 118 | C6H5NH—⌬—OH | 2-OCH3 | m.p. >220° C. | red-brown |

TABLE 2-continued

Compounds of the formula

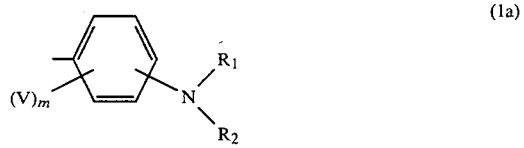

| Comp. No. | X'' | (R4)n | Phys. data | Colour[1] |
|---|---|---|---|---|
| 119 |  | 2,3-(CH3)2 | m.p. 175-82° | red-brown |

[1] Colour in thermography

B. USE EXAMPLES

Example 20:

In order to prepare a dispersion, 2 g of the dicyanomethyleneisoindoline compound (107), 7 g of a 10% aqueous solution of polyvinyl alcohol and 4 g of water are milled in a bead mill for 4 to 5 hours until a particle size of 2-4 μm is reached. The dispersion is separated off from the beads and stored for 18 hours. The dispersion is then knife-coated onto a coating paper having a basis weight of 50 g/m². The coating mixture applied corresponds to a dry weight of 2 g/m².

When using the paper in a fax machine (Infotec 6510), a blue colour develops.

Example 21:

In order to prepare a dispersion A, 2 g of the dicyanomethyleneisoindoline compound (101), 7 g of a 10% aqueous solution of polyvinyl alcohol and 4 g of water are milled in a bead mill for 4 to 5 hours until a particle size of 2-4 μm is reached. The dispersion is separated off from the beads and stored for 18 hours.

In order to prepare a dispersion B, 5 g of triphenylmethane and 12 g of 10% aqueous starch solution are milled together with glass beads until a particle size of 2-4 μm is reached.

2.8 g of dispersion A and 5.8 g of dispersion B are processed to give a coating composition which is applied to a paper having a basis weight of 50 g/m² in such a manner that the coating mixture applied corresponds to a dry weight of 2 g/m².

When using the paper in a fax machine (Infotex 6510), a red-violet colour develops.

What is claimed is:

1. A methylenepyrroline of the formula

in which

X is pyrrolyl, thienyl, indolyl, carbazolyl, acridinyl, pyrazolonyl, benzofuranyl, benzothienyl, naphthothienyl, phenothiazinyl, indolinyl, julolidinyl, kairolinyl, dihydroquinolinyl, tetrahydroquinolinyl, or naphthyl radical which is unsubstituted or substituted by up to three identical or different substituents from the group consisting of halogen, cyano, lower alkyl, $C_5$–$C_6$cycloalkyl, $C_1$–$C_8$acyl-, —$NR_1R_2$, —$OR_3$ or—$SR_3$, or X is an unsubstituted phenyl or a phenyl radical of the formula $$\text{(Ia)}$$

$$\text{(Ib)}$$

in which $R_1$, $R_2$ and $R_3$, independently of one another, are hydrogen, unsubstituted or halogen-, hydroxyl-, cyano- or (lower alkoxy)-substituted alkyl having at most 12 carbon atoms, acyl having 1 to 8 carbon atoms, cycloalkyl having 5 to 10 carbon atoms or unsubstituted or halogen-, trifluoromethyl-, cyano-, (lower alkyl)-, (lower alkoxy)-, (lower alkoxycarbonyl)-, —NX'X''— or 4-NX'X''-phenylamino-ring-substituted phenylalkyl or phenyl, X' and X'', independently of one another, are hydrogen, lower alkyl, cyclohexyl, benzyl or phenyl or $R_1$ and $R_2$ together with the nitrogen atom linking them are a five- or six-membered heterocyclic radical, V is hydroxyl, halogen, lower alkyl, $C_1$–$C_{12}$alkoxy, $C_5$–$C_7$cycloalkoxy, $C_1$–$C_{12}$acyloxy, benzyl, phenyl, benzyloxy or phenoxy each of which is unsubstituted or substituted in the phenyl radical by halogen, cyano, lower alkyl or lower alkoxy, or, in the case of the phenyl radical of formula (1a), also the group —NT₁T₂, T₁ and T₂, independently of one another, are hydrogen, lower alkyl, C₅–C₁₀cycloalkyl, unsubstituted or halogen-, cyano-, (lower alkyl)- or (lower alkoxy)-substituted benzyl, or acyl having 1 to 8 carbon atoms and T₁ is also unsubstituted or halogen-, cyano-, (lower alkyl)- or (lower alkoxy)-substituted phenyl, and m is 0, 1 or 2;

R is CN or substituted or unsubstituted phenylcarbamoyl,

Z is an acyl radical, and

A is a radical for forming an aromatic or heterocyclic ring having 6 ring atoms, it being possible not only for ring A but also for the fused-on ring to be substituted.

2. A methylenepyrroline as claimed in claim 1, in which X is pyrrolyl, pyrazolonyl, indolyl or carbazolyl.

3. A methylenepyrroline as claimed in claim 1, in which X is 2-methylindol-3-yl, N—C₁-C₈alkyl-2-methylindol-3-yl, N—C₂-C₄alkanoyl-2-methylindol-3-yl, 2-phenylindol-3-yl or N—C₁-C₈alkyl-2-phenylindol-3-yl.

4. A pyrroline as claimed in claim 1, in which X is a phenyl or naphthyl radical which is unsubstituted or substituted by up to three identical or different substituents from the group consisting of halogen, cyano, lower alkyl, C₅-C₆cycloalkyl, C₁-C₈acyl, —NR₁R₂, —OR₃ or —SR₃.

5. A pyrroline as claimed in claim 1, in which Z is an acyl group of the formula (1c) Y—(Q₁)ₙ—Q₂—, in which Y is aryl, cycloalkyl, aralkyl or heteroaryl, Q₁ is —NH— or oxygen, Q₂ is —CO— or —SO₂— and n is 0 or 1.

6. A pyrroline as claimed in claim 5, in which Z is an acyl group of the formula Y'—CO— and Y' is C₃-C₈alkyl or phenyl.

7. A pyrroline as claimed in claim 1, in which ring A is a substituted or unsubstituted benzene, naphthalene, pyridine, pyrazine, quinoxaline or quinoline ring.

8. A pyrroline as claimed in claim 1, in which ring A is an unsubstituted or halogen-, methyl-, methoxy-, butoxy-, dimethylamino- or diethylamino-substituted benzene ring.

9. A pyrroline as claimed in claim 1, in which
R is a radical of the formula (1d)

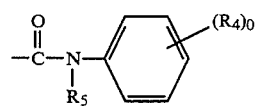

in which each R₄, independently of the others, is hydroxyl, halogen, nitro, cyano, acyl having 1 to 8 carbon atoms, unsubsdtuted or halogen-, hydroxyl-, cyano- or (lower alkoxy)-substituted lower alkyl, or lower alkoxy, R₅ is hydrogen or lower alkyl and o is 0, 1, 2 or 3.

10. An isoindoline as claimed in claim 1, of the formula

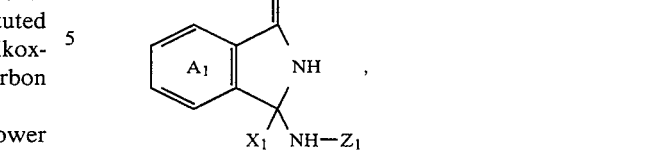

in which A₁ is a benzene ring which is unsubstituted or substituted by halogen, cyano, lower alkyl, lower alkoxy or di(lower alkyl)amino, Z₁ is C₁-C₁₂alkyl—CO— or benzoyl which is unsubstituted or substituted by halogen, nitro, lower alkyl or lower alkoxy and X₁ is a 3-indolyl radical of the formula

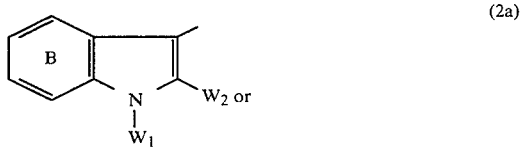

a substituted phenyl radical of the formula

or

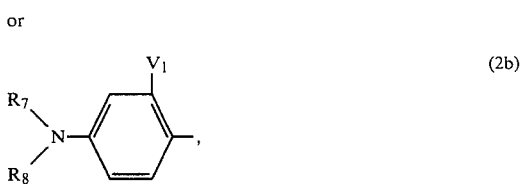

W₁ is hydrogen, unsubstituted or cyano- or (lower alkoxy)-substituted C₁-C₈alkyl, acetyl, propionyl or benzyl, W₂ is hydrogen, lower alkyl, in particular methyl, or phenyl, R₆, R₇ and R₈, independently of one another, are each unsubstituted or hydroxyl-, cyano-or (lower alkoxy)-substituted alkyl having at most 12 carbon atoms, C₅-C₆cycloalkyl, benzyl, phenethyl or phenyl and R₆ is also hydrogen, or (R₅ and R₆) together with the nitrogen atom linking them are pyrrolidino, piperidino or morpholino, V₁ is hydrogen, hydroxyl, halogen, lower alkyl, C₁-C₈alkoxy, benzyloxy or the group —NT₃T₄, T₃ and T₄, independently of one another, are each hydrogen, lower alkyl, lower alkylcarbonyl or unsubstituted or halogen-, methyl- or methoxy-substituted benzoyl R is cyano or a substituted or unsubstituted radical of the formula

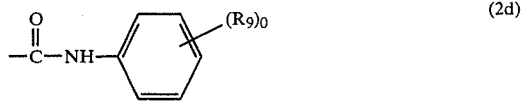

R₉ is halogen or lower alkyl, o is 0, 1 or 2 and

B is unsubstituted or substituted by halogen, lower alkyl, by di(lower alkyl)amino.

11. An isoindoline as claimed in claim 9, in which $X_1$ is a 3-indolyl radical of the formula (2a), $W_1$ is hydrogen or $C_1$-$C_8$alkyl, $W_2$ is methyl or phenyl and $Z_1$ is $C_3$-$C_8$alkylcarbonyl.

12. A dicyanoisoindoline as claimed in claim 1, of the formula

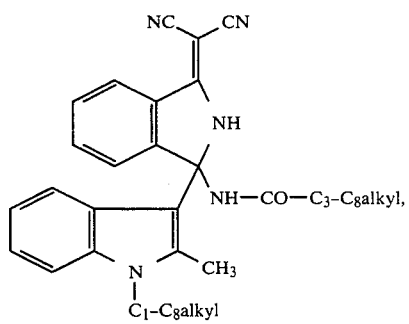
(Ia)

13. A dicyanoisoindoline as claimed in claim 1, of the formula

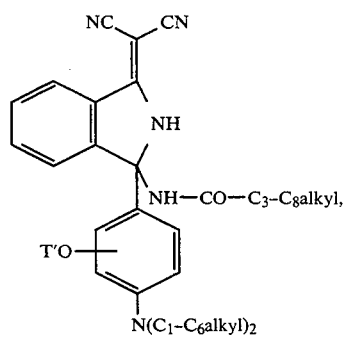
(Ib)

in which T' is hydrogen or $C_1$-$C_6$alkyl.

14. A dicyanoisoindoline as claimed in claim 1, of the formula (Ic)

in which T' is hydrogen or $C_1$-$C_6$alkyl.

15. An isoindoline as claimed in claim 1, of the formula (Id)

in which $R_9$ is halogen or lower alkyl,
o is 0, 1 or 2 and
$V_1$ is hydrogen or hydroxyl.

16. An isoindoline as claimed in claim 1, of the formula (Ie)

in which $R_9$ is halogen, lower alkyl or lower alkoxy,
o is 0, 1 or 2 and
$V_1$ is hydrogen or hydroxyl.

* * * * *